United States Patent [19]

Kameyama et al.

[11] 4,116,972
[45] Sep. 26, 1978

[54] ANTI-INFLAMMATORY 1-OXO-ISOINDOLINE DERIVATIVES AND PROCESSES FOR THEIR PREPARATION

[75] Inventors: Tsutomu Kameyama, Tokyo, Japan; Shigetaka Yoshina, deceased, late of Nagoya, Japan by Teruko Yoshina; Takami Yoshina, heirs at law, Nagoya, Japan

[73] Assignee: Fuji Chemical Industry Company Limited, Kamiichi, Japan

[21] Appl. No.: 720,675

[22] Filed: Sep. 7, 1976

[30] Foreign Application Priority Data

Sep. 11, 1975 [JP] Japan .................................. 50-110692

[51] Int. Cl.$^2$ ............................................. C07D 209/44
[52] U.S. Cl. .................................. 260/326.1; 424/274
[58] Field of Search ..................................... 260/326.1

[56] References Cited

U.S. PATENT DOCUMENTS

| 3,466,297 | 9/1969 | Sulkowski et al. ................ 260/326.1 |
| 3,767,805 | 10/1973 | Carney et al. ....................... 260/326.1 |

*Primary Examiner*—Ethel G. Love
*Attorney, Agent, or Firm*—Flynn & Frishauf

[57] ABSTRACT

Hydrogenated 1-oxo-isoindoline derivatives having a strong anti-inflammatory activity may be prepared by reducing the corresponding hydrogenated 1,3-dioxo-isoindoline derivative to the 3-hydroxy-1-oxo-isoindoline derivative and then further reducing, dehydrating or hydrolizing this compound.

2 Claims, 1 Drawing Figure

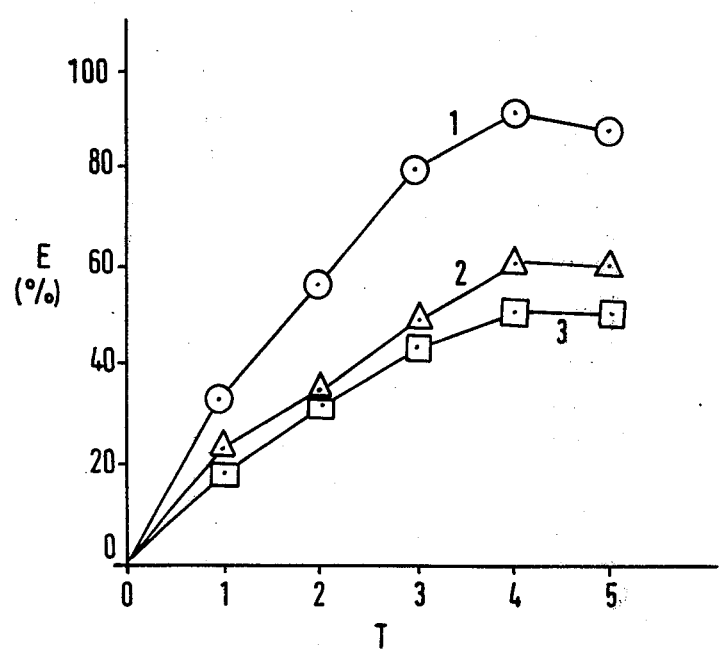

ANTI-INFLAMMATORY 1-OXO-ISOINDOLINE DERIVATIVES AND PROCESSES FOR THEIR PREPARATION

BACKGROUND OF THE INVENTION

The present invention relates to new hydrogenated 1-oxo-isoindoline derivatives, to new processes for their preparation and to their use as anti-inflammatory agents.

For several years, extensive studies of anti-inflammatory agents have been carried out throughout the world, as demand for these agents has increased. Of the anti-inflammatory agents known, including those currently used in therapy, some agents are known to have a strong therapeutic effect. However, known anti-inflammatory agents having a strong therapeutic activity also, in general, exhibit pronounced side-effects; on the other hand, agents whose side-effects are less pronounced and which have a lower toxicity generally have weak therapeutic activity. Such agents, having weak therapeutic activity, must be administered in large quantities, which can give rise to problems during therapy. Thus, either type of agent has both advantages and disadvantages. There is, therefore, a clear need for an agent having strong therapeutic activity but simultaneously weak side-effects and a low toxicity.

We have now discovered that certain hydrogenated 1-oxo-isoindoline derivatives meet these requirements.

BRIEF SUMMARY OF INVENTION

It is, therefore, an object of the present invention to provide a new series of hydrogenated 1-oxo-isoindoline derivatives useful as anti-inflammatory agents having a strong therapeutic effect but relatively weak side-effects.

It is a further object of the invention to provide new processes for the production of the hydrogenated 1-oxo-isoindoline derivatives by the selective reduction of a 1,3-dioxo-isoindoline derivative, followed by reduction, dehydration or hydrolysis of the resulting 3-hydroxy-1-oxo-isoindoline derivative.

The hydrogenated 1-oxo-isoindoline derivatives of the present invention have the general formula (I):

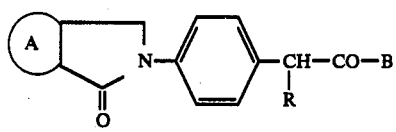

(I)

in which:

A represents a cyclohexane ring which is saturated or contains one or two non-conjugated carbon-carbon double bonds;

R represents a hydrogen atom or an alkyl group having 1, 2 or 3 carbon atoms; and B represents a hydroxyl group, the group —OR$^1$ (in which R$^1$ represents an alkyl group having 1, 2 or 3 carbon atoms) or the group —NR$^2$R$^3$ (in which R$^2$ and R$^3$ are the same or different and each represents a hydrogen atom or an alkyl group having 1, 2 or 3 carbon atoms, or R$^2$ and R$^3$, together with the nitrogen atom to which they are attached, form a non-aromatic heterocyclic group).

BRIEF DESCRIPTION OF DRAWING

The accompanying drawing is a graph showing the oedema ratio, E (a measure of the ability of a compound to reduce the swelling associated with carrageenin-induced oedema), plotted against time after carrageenin injection, for the preferred compound of the invention, α-[4-(1-oxo-4,7-dihydro-2-isoindolinyl)phenyl]propionic acid, in two different doses (curves 2 and 3) and a control (curve 1).

DETAILED DESCRIPTION OF INVENTION

Preferred classes of compounds within the general formula (I) are compounds of formula (Ia):

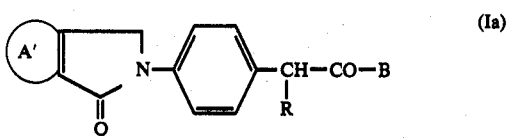

(Ia)

(in which A' represents, together with the 5-membered ring to which it is fused, a 4,7-dihydro-1-oxo-isoindoline or 4,5,6,7-tetrahydro-1-oxo-isoindoline ring system; and R and B are as defined above); and compounds of formula (Ib):

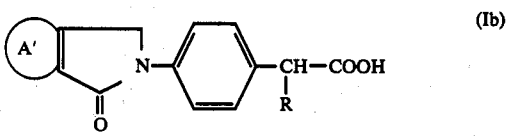

(Ib)

(in which A' and R are as defined above).

In the above formula (I), A preferably represents a cyclohexane, 1-cyclohexene, 4-cyclohexene or 1,4-cyclohexadiene ring. In the above formulae (I) and (Ia), the group B is preferably a hydroxyl group, an alkoxy group having from 1 to 3 carbon atoms (methoxy, ethoxy, propoxy or isopropoxy) or, when B represents the group —NR$^2$R$^3$, an amino, methylamino, ethylamino, propylamino, isopropylamino, dimethylamino, diethylamino, dipropylamino, diisopropylamino, pyrrolidinyl, piperidyl, or morpholino group.

The compounds of the present invention may be prepared as follows:

In a first step, a 1,3-dioxo-isoindoline derivative of general formula (II):

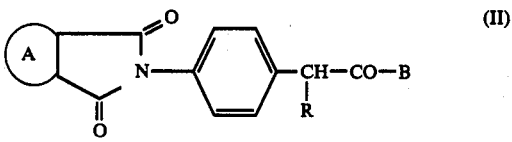

(II)

(in which A, R and B are as defined above) is reacted with a borohydride to convert it to a 3-hydroxy-1-oxo-isoindoline derivative of general formula (III):

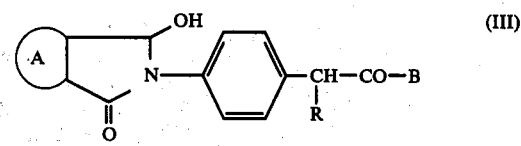

(III)

In a second step, the 3-hydroxy-1-oxo-isoindoline derivative (III) is reduced, dehydrated or hydrolized to give the desired compound of formula (I).

Where the second step of this process consists of hydrolysis, the group —CO—B in compounds (II) and (III) above may be replaced by any group capable of hydrolysis to a carboxylic acid group, and especially it may be replaced by a nitrile group; other preferred groups represented by —CO—B in this case are ester and amido groups.

The first step in the process of the invention involves the selective reduction of one of the carbonyl groups at the 1- or 3- position of the hydrogenated 1,3-dioxo-isoindoline derivative (II) to a hydroxy group. Although a large number of reports showing the partial reduction of aromatic imides, such as phthalimide, have been published, very little is known about the reduction of non-aromatic compounds. Certainly, the reaction conditions employed for the reduction of aromatic imides cannot be applied directly to the reduction of non-aromatic imides.

We have now surprisingly discovered that hydrogenated 1,3-dioxo-isoindoline derivatives of formula (II) may be selectively reduced to the corresponding 3-hydroxy-1-oxo-isoindoline derivatives of formula (III) using a borohydride, such as sodium borohydride, as reducing agent. The amount of borohydride employed will depend upon the compound to be reduced; in the case of the carboxylic acids (B represents a hydroxyl group), a molar excess of borohydride is preferably employed; in the case of the esters, nitriles and amides, the amount of borohydride employed may be less than equimolar with respect to the compound (II) to be reduced.

The reduction with the borohydride can proceed at room temperature, but we prefer to employ an elevated temperature, which depends upon the compound to be reduced. In general, where B represents a hydroxyl group, the optimum temperature is from 50° to 85° C. In the case of esters, amides and nitriles, the optimum temperature is about 50° C.

The reaction is preferably carried out in a solvent, more preferably a polar solvent, in view of the solubility of the compound (II) and the reactivity of the reducing agent. Of the polar solvents, dimethyl sulphoxide is most preferred and gives good results. The esters and nitriles are particularly soluble and only small quantities of solvent are required for these compounds. The reaction begins immediately the reducing agent is added and will generally be complete within several tens of minutes.

In the second step of one embodiment of the process of the present invention, the 3-hydroxy-1-oxo-isoindoline derivative (III) obtained in the first step is further reduced, by conventional techniques, to give the desired compound of formula (I). In this step, the reduction may, for example, be carried out by treating the compound (III) with a metal powder and an acid, preferably an inorganic acid and more preferably a mineral acid. The metallic powder is preferably zinc, tin or iron and the acid is preferably hydrochloric or sulphuric acid. The reaction is preferably carried out at a relatively low temperature, so as to avoid side reactions, temperatures between 10° C. and room temperature being preferred.

We have also found that the 3-hydroxy-1-oxo-isoindoline derivative (III) can easily undergo dehydration, simply by heating, to give a hydrogenated 1-oxo-isoindoline derivative containing a double bond between the 8- and 9-positions; in other words, the dehydration effects 1,3- elimination to give a compound of formula (Ia), as defined above. This dehydration reaction can be carried out to give the hydrogenated 1-oxo-isoindoline derivative (Ia) in very high yield by employing an acidic catalyst, such as acetic acid, hydrochloric acid, sulphuric acid or phosphoric acid. The reaction is preferably carried out in the presence of a solvent, more preferably a polar solvent, such as water, an alcohol (particularly ethanol), dimethylformamide, dimethyl sulphoxide or acetic acid. The reaction is generally complete within from 2 to 3 hours.

The reaction described above may be summarized by the following reaction scheme:

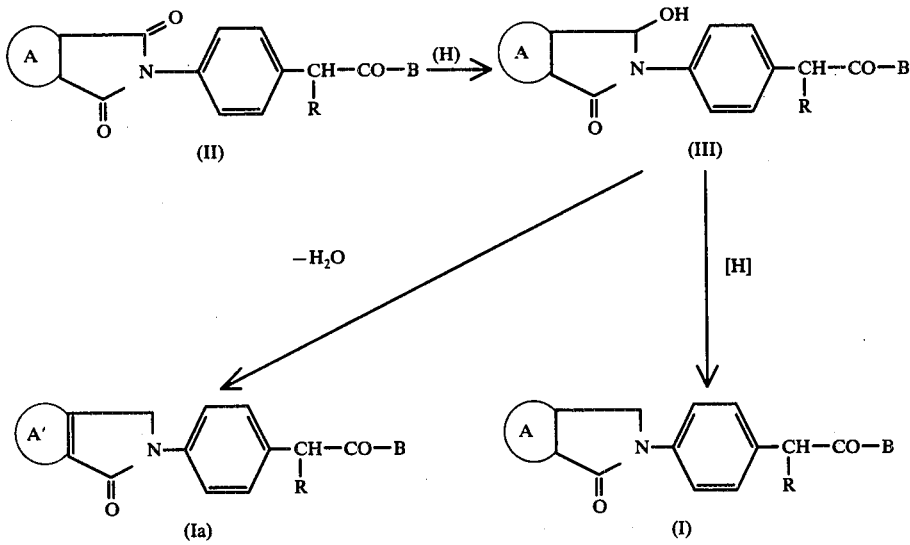

In accordance with a further embodiment of the present invention, we have found that nitriles, esters and amides of the carboxylic acids [compounds (III) wherein B represents a hydroxyl group] may be subjected to hydrolysis to convert the nitrile, ester or amido group to a carboxylic acid group whilst simultaneously the isoindoline ring is subjected to dehydration, to give a compound of formula (Ib), as defined above.

Thus, in accordance with one embodiment of the present invention, there is provided a process which comprises: reducing a 1,3-dioxo-isoindoline derivative of general formula (IIa):

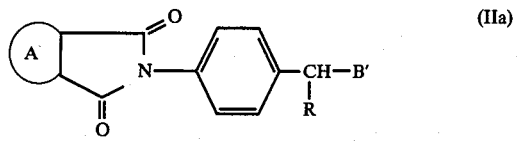

(in which A and R are as defined above and B' represents a nitrile, ester or amide group) with a borohydride compound to produce a 3-hydroxy-1-oxo-isoindoline derivative of general formula (IIIa):

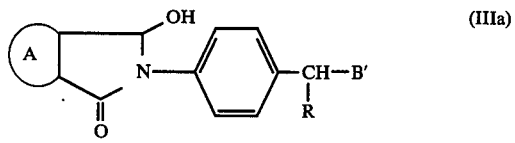

(in which A, R and B' are as defined above); and hydrolizing said 3-hydroxy-1-oxo-isoindoline derivative (IIIa) to produce a hydrogenated 1-oxo-isoindoline derivative of formula (Ib):

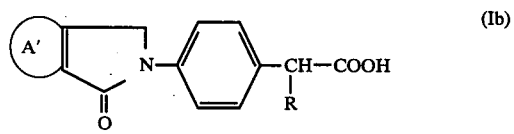

(in which A' and R are as defined above).

The hydrolysis reaction may be effected by methods well-known in the art, e.g. by reaction with an alkali (preferably an alkali metal hydroxide, such as sodium hydroxide), which gives a salt of the desired acid, followed by reaction with an acid (e.g. an inorganic acid such as hydrochloric acid) to give the desired acid itself.

This embodiment of the process of the invention may be summarized by the following reaction scheme:

These salts may be prepared by conventional methods from the carboxylic acids; so too may be prepared the esters and amides from the carboxylic acids of formula (I). Alternatively, the esters and amides of formula (I) [formula (I), B = OR¹ or —NR²R³] may be prepared starting from a corresponding ester or amide of formula (II).

The compounds of formula (II) used as starting materials in the process of the present invention may easily be prepared by condensation of a cycloalkane-1,2-dicarboxylic acid anhydride of general formula (IV):

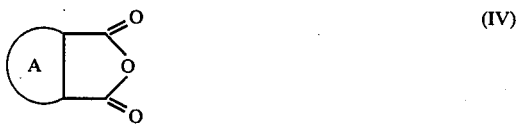

(in which A is as defined above) with an unsubstituted or α-substituted α-(p-aminophenyl)-acetic acid or derivative thereof of formula (V):

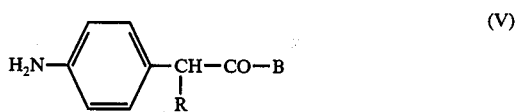

(in which R and B are as defined above). The cycloalkane-1,2-dicarboxylic acid anhydride (IV) and the α-(p-aminophenyl)acetic acid or derivative thereof (V) are preferably reacted together in an equimolar ratio. The reaction is preferably carried out in a solvent, such as acetic acid, and will generally be complete within several hours. Reaction accelerators, such as as pyridine or sodium acetate, may be added to the reaction system to shorten the reaction time but, in most cases, the reaction will proceed quantitatively at reflux temperature without the need for such an accelerator, if acetic acid is used as solvent. Any excess of acetic acid may be removed by evaporation under reduced pressure. The crude hydrogenated 1,3-dioxo-isoindoline derivative (II) thus obtained may be precipitated as impure crystals by addition of water to the residue. This crude product

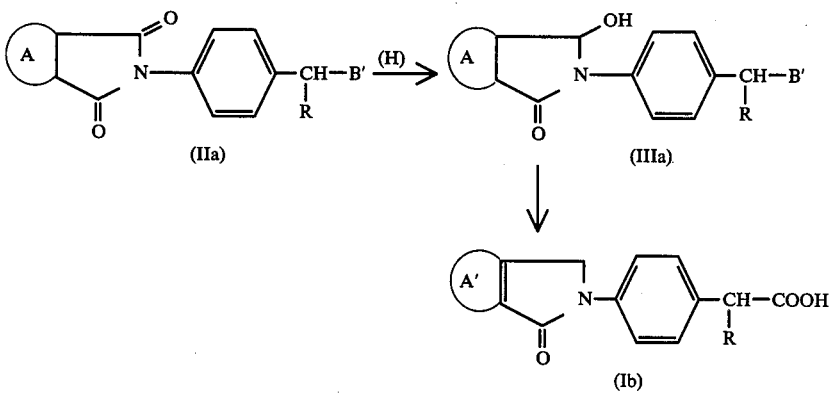

The acids of formula (I) [formula (I) wherein B represents a hydroxyl group] may easily be converted to pharmaceutically acceptable salts by conventional reactions and, accordingly, the present invention thus also consists in pharmaceutically acceptable salts of compounds of fomula (I) wherein B represents a hydroxyl group. Preferred salts are the alkali metal, alkaline earth metal, aluminum and bismuth salts.

may be used directly as a starting material in the process of the invention without any intermediate purification.

The following is a non-limiting list of preferred compounds of the present invention:

1. α-[4-(1-oxo-4,7-dihydro-2-isoindolinyl)phenyl]propionic acid.

2. α-[4-(1-oxo-4,7,8,9-tetrahydro-2-isoindolinyl)-phenyl]propionic acid.
3. 4-(1-oxo-4,5,6,7-tetrahydro-2-isoindolinyl)phenylacetic acid.
4. 4-(1-oxo-hexahydro-2-isoindolinyl)phenylacetic acid.
5. α-[4-(1-oxo-hexahydro-2-isoindolinyl)phenyl]propionic acid.
6. 4-(1-oxo-4,7-dihydro-2-isoindolinyl)phenylacetic acid.
7. Aluminium α-[4-(1-oxo-4,7-dihydro-2-isoindolinyl)phenyl]propionate.
8. Bismuth α-[4-(1-oxo-4,7-dihydro-2-isoindolinyl)phenyl]propionate.
9. Ethyl α-[4-(1-oxo-4,7-dihydro-2-isoindolinyl)phenyl]propionate.
10. α-[4-(1-oxo-4,7-dihydro-2-isoindolinyl)phenyl]propionamide
11. α-[4-(1-oxo-4,7-dihydro-2-isoindolinyl)phenyl]propionic acid morpholide.
12. α-[4-(1-oxo-4,7-dihydro-2-isoindolinyl)phenyl]propionic acid diethylamide.
13. Sodium α-[4-(1-oxo-4,7-dihydro-2-isoindolinyl)phenyl]propionate.
14. α-[4-(1-oxo-4,5,6,7-tetrahydro-2-isoindolinyl)phenyl]propionic acid.

The compounds of the present invention have been shown to have an inhibitory effect on carrageenin-induced oedema, which is the standard test for anti-inflammatory activity. For example, α-[4-(1-oxo-4,7-dihydro-2-isoindolinyl)phenyl]propionic acid (Compound 1) shows a particularly strong inhibitory effect on oedema induced by the injection of carrageenin into the hind foot of a rat, the $ED_{50}$ (effective dose 50%) thereof being 11.1 mg/kg (4.0–30.9 mg/kg). In addition, the $LD_{50}$ (lethal dose 50%), which is a measure of acute toxicity, is as high as 328 mg/kg (oral administration to a male rat). Thus, the therapeutic index ($LD_{50}/ED_{50}$) is 29.55. The therapeutic index is a measure of the safety of a compound for use in therapy and the high value of the therapeutic index of α-[4-(1-oxo-4,7-dihydro-2-isoindolinyl)phenyl]propionic acid shows that this compound is of considerable therapeutic value. Moreover, the compounds of the invention have only a small effect on the stomach and intestinal tract, although such effects are often noted as side-effects of other anti-inflammatory agents.

The compounds of formula (I) and their pharmaceutically acceptable salts can be administered orally or parenterally by conventional methods. Accordingly, the compounds may be formulated as pharmaceutical compositions for oral or parenteral administration, using solid or liquid pharmaceutical carriers and diluents, and optionally also appropriate pharmaceutical adjuvants, for example as tablets, capsules, injectible liquids and suspensions. The optimum dosage will vary, depending on the age, body weight and clinical condition of the patients.

Since most of the compounds of formula (I) are crystalline and easy to handle, they are very convenient to formulate as pharmaceutical compositions; where, however, the compounds of formula (I) are not convenient to handle, their pharmaceutically acceptable salts may be employed.

The pharmacological properties of the compounds of the invention, and particularly of Compound 1, α-[4-(1-oxo-4,7-dihydro-isoindolinyl)phenyl]propionic acid, are illustrated by the following tests:

1. ANTI-INFLAMMATORY ACTIVITY

Carrageenin-oedema test in rats

Compound 1 was administered through a stomach tube, in suspension in a 0.3% by weight carboxymethylcellulose aqueous solution, in an amount of 6.25 mg/kg or 12.5 mg/kg to male rats of the Wistar strain having a body weight of 120–130 g. After 1 hour, inflammation was induced by injecting subcutaneously 1 ml of a 1% carrageenin suspension into the plantar tissue of the right hind paw of each rat. Paw oedema was measured volumetrically, immediately before and also every hour for 5 hours after the carrageenin injection, and the response, measured as the oedema effect (E) was calculated by the following equation:

$$E = (V_T - V_o)/V_o$$

where $V_o$ and $V_T$ represents the paw volumes $O$ and $T$ after the carrageenin injection, respectively.

The tests were also carried out on a control group of rats to which no anti-inflammatory agent had been administered. Each test was carried out on a group of six rats.

The results obtained are summarized by the accompanying drawing, which shows a graph of the oedema ratio, E%, against the time T (hours) after the carrageenin injection. Curve 1 shows the results obtained with the control group, Curve 2 shows the results obtained with the group to which Compound 1 was administered in an amount of 6.25 mg/kg, and Curve 3 shows the results obtained with the group to which Compound 1 was administered in an amount of 12.5 mg/kg.

An inhibitory effect resulting from the administration of Compound 1 had clearly appeared at the end of the first hour after carrageenin injection and a strong inhibitory effect appeared over the first 5 hours. The inhibitory effect was measured by the inhibitory ratio (IR), calculated from the following equation:

$$IR = [(E_c - E)/E] \times 100\ (\%)$$

where $E_c$ represents the oedema ratio of the control rats and $E$ represents the oedema ratio of the rats treated with Compound 1.

The inhibitory ratio was determined on administration of various amounts of Compound 1 and the results obtained 3 hours after carrageenin injection are shown in Table 1.

Table 1

| Amount administered (mg/kg) | Inhibitory ratio (%) |
|---|---|
| 5 | 33.2 |
| 10 | 57.1 |
| 20 | 64.7 |
| 40 | 69.0 |

From the results given in Table 1, it can be seen that the inhibitory effect 3 hours after carrageenin injection increased in rough proportion to the amount of Compound 1 administered.

From the results obtained during this test, it was calculated that the $ED_{50}$ was 11.1 mg/kg (4.0–30.9 mg/kg).

2. ANALGESIC EFFECT

The analgesic effect of Compound 1 was tested on male rats of the Wistar strain, with a body weight of about 90 g. The rats were tested in groups of six. Only those animals having a normal pain threshold in both hind legs were selected for the tests. The compound to be tested was suspended in 0.3% carboxymethylcellulose aqueous solution and administered orally. Compound 1 was tested in the amounts shown in Table 2 as were other known anti-inflammatory agents. The analgesic activity was tested by the Pressure Method [Brit. J. Pharmac., 6, 572 (1951)] the Acetic Acid Raising Method [Proc. Soc. Exp. Biol. Med. 118, 763, (1965)] and the Randall-Selitto Method [Arch. Int. Pharmacodyn., 111, 409, (1957)]. The data obtained are shown in Table 3. Although the analgesic effect of the compound of the invention is weak, an effect was observed.

Table 2

| Compound tested | Amount (mg/kg) administered orally | Pressure method Ratio (average) | Acetic Acid Raising method* a | b | Amount (mg/kg) administered orally | Randall-Selitto method Analgesic index Inflamed foot | Normal foot |
| --- | --- | --- | --- | --- | --- | --- | --- |
| Compound 1 | 100 | — | 21.0 | 7 | 10 | 1.21 | 1.04 |
| Compound 1 | 150 | 1.36 | — | — | — | — | — |
| Ketoprofen | 100 | 1.40 | 53.8 | 60 | 10 | 1.20 | 1.03 |
| Phenylbutazone | 200 | — | 25.8 | 20 | 100 | 1.37 | 1.11 |
| Ibuprofen | 200 | — | 21.9 | 20 | 100 | 1.20 | 1.05 |
| Mefenamic acid | 150 | — | 45.4 | 60 | — | — | — |
| Aminopyrine | 150 | 2.02 | — | — | — | — | — |

*
a = graded response
b = all or none response

3. ACUTE TOXICITY

Compound 1 was administered in the amounts shown in Table 3 to male rats of the Wistar strain having a body weight of 110–130 g. The rats were tested in groups of eight and similar tests were applied to similar groups of female rats. The compound to be tested was suspended in a 0.3% aqueous solution of carboxymethylcellulose and was administered through a stomach tube. The lethal dose 50% ($LD_{50}$) and credibility limit 95% (CL) were calculated from the lethal effect by the method of Litchield and Wilcoxon [J. Pharmac. Exp. Ther., 96, 99 (1949)]; the lethal effect was expressed as X/n, in which X is the number of animals which were dead one week after administration and n is the total number of animals used in the test. The results are shown in Table 3.

Table 3

| Amount orally administered (mg/kg) | Lethal effect Male | Female | $LD_{50}$ (95% CL) Male | Female |
| --- | --- | --- | --- | --- |
| 180 | 0/8 | 1/8 | | |
| 234 | 2/8 | 2/8 | 328 mg/kg | 345 mg/kg |
| 304 | 4/8 | 3/8 | | |
| 395 | 5/8 | 5/8 | (238–453) | (250–476) |
| 514 | 6/8 | 6/8 | | |
| 668 | 8/8 | 8/8 | | |

4. EFFECT ON GASTRIC ULCER

Male rats of the Donryu strain having a body weight of 150–200 g were starved for 24 hours and the effects of administration of Compound 1 and its aluminium salt (Compound 7) on the occurrence of gastric ulcers were determined, as were the effects of other known anti-inflammatory agents.

Each compound to be tested was suspended in a 0.3% solution of carboxymethylcellulose in physiological saline and administered in an amount of 1 ml per 200 g body weight of the rat. Determination of the occurrence of gastric inflammation and ulceration was calculated by adding the sizes of ulcerated regions ($mm^2$) of each rat observed within a lattice (width 1 cm, divided into 10 equal parts) of a stereomicroscope. The determination was made on the stomach removed after sacrifice of the animal and then fixed for 10 minutes with 1% formalin.

In a first method, the compound to be tested was administered orally after 24 hours starvation and then, after a further 18 hours, the animal was sacrificed, under ether anaesthesia. The degree of ulceration was determined as described above and the results achieved are shown in Table 4.

Table 4

| Compound tested | Number of animals | Amount administered (mg/kg P.O.) | Size($mm^2$) of ulcerated region of stomach |
| --- | --- | --- | --- |
| Phenylbutazone | 10 | 200 | 6.6 ± 1.31 |
| Aspirin | 10 | 200 | 9.7 ± 1.36 |
| Indomethacin | 10 | 20 | 8.0 ± 1.22 |
| Compound 1 | 10 | 50 | 4.1 ± 0.46 |
| Compound 7 | 10 | 50 | 2.4 ± 0.49** |
| Control | 10 | — | 0.8 ± 0.19 |

**Observed significant difference at $p = 0.01$ (Determination based on difference between average values of groups administered the compound and phenylbutazone)

As a second method, first oral administration was effected after 24 hours starvation and a second oral administration was effected after a further 12 hours starvation. Each animal was then sacrificed, under ether anaesthesia, 6 hours after the second administration. The degree of ulceration was then determined as described above and the results are shown in Table 5. This method was employed to observe the effect after repeated administration of the compounds of the invention.

Table 5

| Compound tested | Number of animals | Amount administered (mg/kg P.O.) | Size(mm²) of ulcerated region of stomach |
|---|---|---|---|
| Phenyl-butazone | 10 | 200 × 2 | 17.2 ± 1.93 |
| Aspirin | 10 | 200 × 2 | 27.2 ± 3.01* |
| Indomethacin | 10 | 20 × 2 | 15.3 ± 1.20 |
| Compound 1 | 10 | 50 × 2 | 11.3 ± 2.00* |
| Compound 7 | 10 | 50 × 2 | 10.3 ± 1.00** |
| Control | 9 | — | 1.0 ± 0.54 |

*Observed significant difference at p = 0.01 (Determination based on difference between average values of groups administered the compound and phenylbutazone)
**Observed significant difference at p = 0.1 (as above)

As shown in tables 4 and 5, the effect of the compounds of the invention on the stomach was relatively weak and apparently weaker than that of Indomethacin.

PREPARATIVE EXAMPLES

The preparation of the compounds of the invention is illustrated by the following non-limiting Examples.

EXAMPLE 1

α-[4-(1-oxo-4,7-dihydro-2-isoindolinyl)phenyl]propionic acid (Compound 1)

(a) 75.5 g (0.5 mole) of cis-4-cyclohexene-1,2-dicarboxylic acid anhydride were added to 600 ml of glacial acetic acid and there were then added to the mixture 82.5 g (0.5 mole) of α-(p-aminophenyl)propionic acid. The resulting mixture was refluxed with heating for 20 hours. After the reaction was complete, the mixture was added to water. The crystals which precipitated were collected by filtration, dried and recrystallized from ethanol yielding quantitatively α-[4-(1,3-dioxo-4,7,8,9-tetrahydro-2-isoindolinyl)phenyl]propionic acid (135.0 g), melting point 191°–193° C.

(b) 15.0 g (0.05 mole) of the α-[4-(1,3-dioxo-4,7,8,9-tetrahydro-2-isoindolinyl)phenyl]propionic acid obtained in (a) above were added to 70 ml of dimethyl sulphoxide, and the mixture was heated to 60° C. To the mixture were then added, with stirring, over 10 minutes 3.8 g (0.1 mole) of sodium borohydride, and the resulting mixture was then heated to 85° C. and maintained at that temperature for 45 minutes. When the reaction was complete, the mixture was poured into ice-water and acidified with dilute hydrochloric acid. The acidified mixture was salted out and extracted with ethyl acetate. The solvent was then removed from the extract by evaporation under reduced pressure, giving α-[4-(3-hydroxy-1-oxo-4,7,8,9-tetrahydro-2-isoindolinyl)phenyl]propionic acid, as an oil.

(c) The oil obtained in step (b) above was added as such to 200 ml of 3.5% aqueous hydrochloric acid and the mixture was refluxed, with heating, for 2 hours. The crystals which precipitated were collected by filtration, dried and crystallized from isopropyl alcohol, giving 9.0 g (yield 65.0%) of α-[4-(1-oxo-4,7-dihydro-2-isoindolinyl)phenyl]propionic acid, melting point 220°–221.5° C.

The structure of the product was confirmed by the following analytical data:

Mass spectrum: 283 M⁺ (molecular ion peak).

IR spectrum (KBr) cm⁻¹: 3100–2500 (—COOH), 1710 (—CO—), 1640 (—CON—).

NMR spectrum (dimethyl sulphoxide - d₆).

| τ | | | Proton ratio |
|---|---|---|---|
| 3.40 | phenyl | doublet | 28 cps. |
| 3.81 | phenyl | doublet | 28 cps. |
| 3.80 | —COOH | singlet (broad) | 1 |
| 4.22 | vinyl | singlet (broad) | 2 ( 5- & 6-positions) |
| 5.65 | methylene | singlet | 2 (3-position) |
| 6.38 | methine | quartet | 1 |
| 7.04 | methylene | doublet(broad) | 27 cps. ⎫ 4- & 7- |
| 7.20 | methylene | doublet(broad) | 27 cps. ⎭ positions |
| 8.64 | methyl | doublet | 37 cps. |

Elemental analysis: Calculated: H, 6.05%; C, 72.06%; N, 4.94% Found: H, 6.00%; C, 72.09%; N, 4.99%

The structure of the compound was thus confirmed to be:

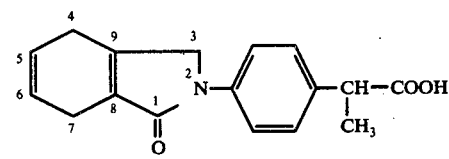

EXAMPLE 2

α-[4-(1-oxo-4,7-dihydro-2-inoindolinyl)phenyl]propionic acid (Compound 1)

(a) Oily α-[4-(3-hydroxy-1-oxo-4,7,8,9-tetrahydro-2-isoindolinyl)phenyl]propionic acid, prepared as described in step (b) of Example 1, was added to water and, after washing thoroughly, was extracted with ethyl acetate. The extract was washed successively with dilute aqueous sodium hydrogen carbonate solution and then water. After drying the extract over sodium sulphate, the solvent was removed by evaporation under reduced pressure over a gentle heat, giving, as a crystalline residue, 5.0 g (yield 33.3%) of α-[4-(3-hydroxy-1-oxo-4,7,8,9-tetrahydro-2-isoindolinyl)phenyl]propionic acid, decomposing at 82°–85° C.

(b) 5.0 g (0.0166 mole) of the compound obtained above were then added to 50 ml of 3.5% aqueous hydrochloric acid and the mixture was refluxed, with heating, for 2–3 hours. Crystals spontaneously precipitated although, if they do not, they may be obtained by evaporation under reduced pressure. These crystals were washed with water, dried and crystallized from isopropyl alcohol, giving 3.8 g (81.0%) of α-[4-(1-oxo-4,7-dihydro-2-isoindolinyl)phenyl]propionic acid, melting point 220°–221.5° C. The identity of this compound with that produced in Example 1 was established by melting point determination of a mixture of the compounds.

EXAMPLE 3

α-[4-(1-oxo-4,7,8,9-tetrahydro-2-isoindolinyl)phenyl]propionic acid (Compound 2)

3.0 g (0.01 mole) of α-[4-(3-hydroxy-1-oxo-4,7,8,9-tetrahydro-2-isoindolinyl)phenyl]propionic acid, prepared as described in step (a) of Example 2, were added to 20 ml of acetic acid and the mixture was maintained at 20° C. 3.92 g of zinc powder were added, with stirring, to the solution, after which 9 ml of concentrated hydrochloric acid were added dropwise to the mixture, over about 10 minutes, maintaining the temperature at 20° C. 30 minutes after the addition was complete, a further 9 ml of concentrated hydrochloric acid were added to the mixture under the same conditions. After completion of this addition, the resulting mixture was stirred at 20° C. for 3 hours.

At the end of this time, the excess zinc was filtered off and the filtrate was added to water. The resulting aqueous solution was extracted with ethyl acetate. The extract was washed successively with water, with a dilute aqueous solution of sodium hydrogen carbonate and again with water. The extract was then dried over anhydrous sodium sulphate and the solvent was evaporated off under reduced pressure. The residue thus obtained was dissolved in a small amount of chloroform and purified by column chromatography using a silica gel (Wako-gel C-200) column (2cm diameter, 18 cm long) using benzene as the eluent. The desired α-[4-(1-oxo-4,7,8,9-tetrahydro-2-isoindolinyl)phenyl]propionic acid was collected. This compound melted at 110°–113° C. Upon recrystallization from a mixture of acetone and petroleum ether, there were obtained 0.5 g (17.5%) of crystals melting at 115°–116° C.

The structure was confirmed by elemental analysis, mass spectroscopy, infra-red spectroscopy and NMR spectroscopy:

Mass spectrum: 285 M+ (molecular ion peak).
IR spectrum cm$^{-1}$: 3100–2500 (OH), 1700 (C=O).

EXAMPLE 4

4-(1-oxo-4,5,6,7-tetrahydro-2-isoindolinyl)phenylacetic acid (Compound 3)

(a) Equimolar amounts of cyclohexane-1,2-dicarboxylic acid anhydride and p-aminophenylacetic acid were reacted as described in step (a) of Example 1, yielding quantitatively 4-(1,3-dioxo-hexahydro-2-isoindolinyl)phenylacetic acid (melting point 219°–221° C.).

(b) 00.2 mole of the 4-(1,3-dioxo-hexahydro-2-isoindolinyl)phenylacetic acid thus obtained was dissolved in 20 ml of dimethyl sulphoxide. The resulting mixture was reduced with 1.14 g (0.03 mole) of sodium borohydride, as described in step (b) of Example 1, and was then poured into ice-water. The mixture was acidified with dilute hydrochloric acid, to precipitate crystals. These crystals were collected by filtration, dried and recrystallized from a mixture of ethanol and petroleum ether, giving 5.0 g (86.2%) of 4-(3-hydroxy-1-oxo-hexahydro-2-isoindolinyl)phenylacetic acid, decomposing at 145° C.

The structure of this compound was determined by elemental analysis, mass spectroscopy, infra-red spectroscopy and NMR spectroscopy.

Mass spectrum: 289 M+ (molecular ion peak).

(c) To 20 ml of acetic acid were added 2.87 g (0.01 mole) of the 4-(3-hydroxy-1-oxo-hexahydro-2-isoindolinyl)phenylacetic acid prepared in step (b) above. The mixture was refluxed, with heating, for 2 hours and the solvent was then evaporated off under reduced pressure, leaving a crystalline residue. These crystals were washed with water, dried and recrystallized from a mixture of ethanol and petroleum ether, giving 2.5 g (89%) of 4-(1-oxo-4,5,6,7-tetrahydro-2-isoindolinyl)phenylacetic acid, melting point 189°–191° C.

The structure was confirmed by elemental analysis, mass spectroscopy, infra-red spectroscopy and NMR spectroscopy.

Mass spectrum: 271 M+ (molecular ion peak).

EXAMPLE 5

α-[4-(1-oxo-4,5,6,7-tetrahydro-2-isoindolinyl)phenyl]propionic acid (Compound 14)

(a) Equimolar amounts of cyclohexane-1,2-dicarboxylic acid anhydride and α-(p-aminophenyl)propionic acid were treated as described in step (a) of Example 1, to yield quantitatively α-[4-(1,3-dioxo-hexahydro-2-isoindolinyl)phenyl]propionic acid, melting point 224°–226° C.

(b) Proceeding as described in step (b) of Example 4, 6.0 g (0.02 mole) of this α-[4-(1,3-dioxohexahydro-2-isoindolinyl)phenyl]propionic acid were reduced and subsequently treated to give crystals. These were recrystallized from a mixture of acetone and petroleum ether, yielding 5.7 g (90%) of α-[4-(3-hydroxy-1-oxo-hexahydro-2-isoindolinyl)phenyl]propionic acid, decomposing at 162° C. The structure was determined by elemental analysis, mass spectroscopy, infra-red spectroscopy and NMR spectroscopy.

Mass spectrum: 303 M+ (molecular ion peak).

(c) Following the procedure described in step (c) of Example 4, 3.0 g (0.001 mole) of the α-[4-(3-hydroxy-1-oxo-hexahydro-2-isoindolinyl)phenyl]propionic acid produced in step (b) above were converted to α-[4-(1-oxo-4,5,6,7-tetrahydro-2-isoindolinyl)phenyl]propionic acid. On recrystallizing this compound from ethanol, there were obtained 2.4 g (80%) of crystals melting at 182°–184° C.

The structure of this compound was determined by elemental analysis, mass spectroscopy, infra-red spectroscopy and NMR spectroscopy.

Mass spectrum: 285 M+ (molecular ion peak).

EXAMPLE 6

4-(1-oxo-hexahydro-2-isoindolinyl)phenylacetic acid (Compound 4)

Following the procedure described in Example 3, 2.87 g (0.01 mole) of 4-(3-hydroxy-1-oxo-hexahydro-2-isoindolinyl)phenylacetic acid [prepared as described in step (b) of Example 4] were reduced to 4-(1-oxo-hexahydro-2-isoindolinyl)phenylacetic acid. After removal of excess zinc by filtration, the crystals precipitated upon addition of water were collected by filtration, washed with water, dried and recrystallized from a mixture of ethanol and petroleum ether. There were obtained 2.2 g (80%) of the desired compound, melting at 157°–159° C. The structure of the compound was confirmed by elemental analysis, mass spectroscopy, infra-red spectroscopy and NMR spectroscopy.

Mass spectrum: 273 M+ (molecular ion peak).

EXAMPLE 7

α-[4-1(-oxo-hexahydro-2-isoindolinyl)phenyl]propionic acid (Compound 5)

Following the procedure described in Example 3, 3.0 g (0.01 mole) of α-[4-(3-hydroxy-1-oxo-hexahydro-2-isoindolinyl)phenyl]propionic acid [prepared as described in step (b) of Example 5] were reduced to α-[4-(1-oxo-hexahydro-2-isoindolinyl)phenyl]propionic acid. After removal of excess zinc by filtration, crystals were precipitated by addition of water and were collected by filtration, washed with water, dried and recrystallized from ethanol. There were obtained 2.5 g (86.0%) of the desired compound, melting at 147°–148.5° C. The structure of the compound was confirmed by elemental anal-

EXAMPLE 8

4-(1-oxo-4,7-dihydro-2-isoindolinyl)phenylacetic acid (Compound 6)

Following the procedure described in step (a) of Example 1, 9.1 g (0.06 mole) of cis-4-cyclohexene-1,2-dicarboxylic acid anhydride and 9.0 g (0.06 mole) of p-aminophenylacetic acid were reacted together to yield quantitatively 15.4 g of 4-(1,3-dioxo-4,7,8,9-tetrahydro-2-isoindolinyl)phenylacetic acid, melting at 174°–176° C. upon recrystallization from ethanol.

Following the procedures of steps (b) and (c), respectively, of Example 1, this compound was reduced with sodium borohydride to yield 4-(3-hydroxy-1-oxo-4,7,8,9-tetrahydro-2-isoindolinyl)phenylacetic acid, which was then dehydrated to give 4-(1-oxo-4,7-dihydro-2-isoindolinyl)phenylacetic acid. Upon recrystallization from ethanol, 7.8 g (50%) of crystals, melting at 198°–200° C., were obtained. The structure of the compound thus obtained was confirmed by elemental analysis, mass spectroscopy, infra-red spectroscopy and NMR spectroscopy.

Mass spectrum: 269 M+ (molecular ion peak).

EXAMPLE 9

α-[4-(1-oxo-4,7-dihydro-2-isoindolinyl)phenyl]propionic acid (Compound 1)

To a mixture of 3.0 g (0.01 mole) of α-[4-(1,3-dioxo-4,7,8,9-tetrahydro-2-isoindolinyl)phenyl]propionic acid [prepared as described in step (a) of Example 1], 150 ml of ethanol and 210 ml of dioxan in a flask equipped with a cooler, a stirred and a thermometer was added 0.02 mole of sodium borohydride; the resulting mixture was warmed at 25° C. for 4 hours and then poured into ice-water. This was acidified with dilute hydrochloric acid and extracted with ethyl acetate. The extract was concentrated by evaporation under reduced pressure, leaving a residue which, after mixing with 40 ml of 5% by weight aqueous hydrochloric acid, was refluxed, with heating and stirring, for 3 hours. After cooling, crystals precipitated; these were collected by filtration and washed well with water. The crystals were then separated and purified using a silica gel column; there were obtained 0.08 g (10%) of Compound 1, melting point 220°–221.5° C.

EXAMPLE 10

α-[4-(1-oxo-4,7-dihydro-2-isoindolinyl)phenyl]propionic acid (Compound 1)

A mixture of 3.2g (0.01 mole) of ethyl α-[4-(1,3-dioxo-4,7,8,9-tetrahydro-2-isoindolinyl)phenyl]propionate [prepared substantially as described in step (a) of Example 1 but using ethyl α-(p-aminophenyl)propionate] and 6 ml of dimethyl sulphoxide was warmed to 50° C. in a flask equipped with a stirrer and a thermometer; 0.19 g (0.005 mole) of sodium borohydride was then added to the mixture over a period of 10 minutes. This mixture was then warmed at 50° C. for a further 5.5 hours. The reaction mixture was then poured into ice-water, which was then acidified with dilute hydrochloric acid and extracted with ethyl acetate. The solvent was removed from the extract by evaporation under reduced pressure and the resulting residue was, after adding 50 ml of 3.5% by weight aqueous hydrochloric acid, refluxed by warming, with stirring, for 2 hours. After cooling, the crystals which precipitated were collected by filtration, washed well with water, dried and recrystallized from isopropyl alcohol, giving 1.8 g (65%) of α-[4-(1-oxo-4,7-dihydro-2-isoindolinyl)phenyl]propionic acid, melting point 220°–221.5° C.

EXAMPLE 11

4-(1-oxo-4,5,6,7-tetrahydro-2-isoindolinyl)phenylacetic acid (Compound 3)

A mixture of 3.1 g (0.01 mole) of ethyl 4-(1,3-dioxohexahydro-2-isoindolinyl)phenyl acetate and 6 ml of dimethyl sulphoxide was warmed to 50° C. in a flask equipped with a stirrer and a thermometer; 0.19 g (0.005 mole) of sodium borohydride was then added to the mixture over a period of 10 minutes. The mixture was then warmed at 50° C. for a further 5.5 hours. At the end of this time, the reaction mixture was poured into ice-water, which was then acidified with dilute hydrochloric acid and extracted with ethyl acetate. The solvent was removed from the extract by evaporation under reduced pressure, leaving a residue which, after addition of 50 ml of 3.5% by weight aqueous hydrochloric acid, was refluxed by heating, with stirring, for 2 hours. On cooling, crystals precipitated; these were collected by filtration, washed well with water, dried and recrystallized from a mixture of ethanol and petroleum ether, to give 1.9 g (70%) of 4-(1-oxo-4,5,6,7-tetrahydro-2-isoindolinyl)-phenylacetic acid.

EXAMPLE 12

α-[4-(1-oxo-4,7,8,9-tetrahydro-2-isoindolinyl)phenyl]propionic acid (Compound 2)

A mixture of 16 g (0.05 mole) of ethyl α-[4-(1,3-dioxo-4,7,8,9-tetrahydro-2-isoindolinyl)phenyl]propionate and 30 ml of dimethyl sulphoxide was warmed to 50° C. in a flask equipped with a stirrer and a thermometer. 1 g (0.025 mole) of sodium borohydride was then added to the mixture over a period of 10 minutes, after which the mixture was heated for a further 5.5 hours at 50° C. After this, the reaction mixture was poured into ice-water, which was then acidified with dilute hydrochloric acid and extracted with ethyl acetate. The solvent was removed from the extract by evaporation under reduced pressure, to leave a residue. 150 ml of acetic acid and 19 g (0.3 mole) of zinc were added to the residue. Then maintaining the temperature at a value not above 20° C., 100 ml of concentrated hydrochloric acid were added dropwise, with stirring, to the mixture over a period of 30 minutes. The mixture was allowed to react at 20° C. for 3 hours and was then extracted with ethyl acetate. The solvent was removed from the extract by evaporation under reduced pressure to leave a residue which, after addition of 200 ml of ethanol, 100 ml of water and 16 g of potassium carbonate, was refluxed by warming, with stirring, for 2 hours. After cooling the mixture, it was acidified with dilute hydrochloric acid and the crude crystals which precipitated as a result were separated and purified using a silica gel column, yielding 1.4 g (10%) of α-[4-(1-oxo-4,7,8,9-tetrahydro-2-isoindolinyl)phenyl]propionic acid, melting point 115°–116° C.

EXAMPLE 13

α-[4-(1-oxo-4,7-dihydro-2-isoindolinyl)phenyl]propionic acid (Compound 1)

A mixture of 2.8 g (0.01 mole) of α-[4-(1,3-dioxo-4,7,8,9-tetrahydro-2-isoindolinyl)phenyl]propionitrile and 8 ml of dimethyl sulphoxide was warmed to 50° C. in a flask equipped with a stirrer and a thermometer; after adding 0.19 g (0.005 mole) of sodium borohydride over a period of 10 minutes, the mixture was further warmed at 50° C. for 6 hours. The reaction mixture was then poured into ice-water, and acidified with dilute hydrochloric acid; the mixture was then extracted with ethyl acetate. The solvent was removed from the extract by evaporation under reduced pressure, leaving a residue which, after addition of 50 ml of concentrated hydrochloric acid, was refluxed by heating, with stirring, for 3 hours. When the reaction was complete, the reaction mixture was poured into ice-water and the crystals which were produced were collected by filtration, washed well with water, dried and recrystallized from isopropyl alcohol. There were obtained 2.2 g (80%) of α-[4-(1-oxo-4,7-dihydro-2-isoindolinyl)phenyl]propionic acid, melting point 220°–221.5° C.

EXAMPLE 14

4-(1-oxo-4,7-dihydro-2-isoindolinyl)phenylacetic acid (Compound 6)

A mixture of 2.8 g (0.01 mole) of 4-(1,3-dioxo-4,7,8,9-tetrahydro-2-isoindolinyl)phenylacetonitrile and 8 ml of dimethyl sulphoxide was warmed to 50° C. in a flask equipped with a stirrer and a thermometer. 0.19 g (0.005 mole) of sodium borohydride were added to the mixture over a period of 10 minutes and the mixture was then warmed at 50° C. for 6 hours. The reaction mixture was then poured into ice-water and, after acidification with dilute hydrochloric acid, was extracted with ethyl acetate. The solvent was removed from the extract by evaporation under reduced pressure, leaving a residue which, after addition of 50 ml of concentrated hydrochloric acid, was refluxed by heating, with stirring, for 3 hours. The mixture was then poured into ice-water and the resulting crystals were collected by filtration, washed well with water, dried and recrystallized from ethanol, giving 1.5 g (60%) of 4-(1-oxo-4,7-dihydro-2-isoindolinyl)phenylacetic acid, melting point 198°–200° C.

EXAMPLE 15

4-(1-oxo-hexahydro-2-isoindolinyl)phenylacetic acid (Compound 4)

A mixture of 13.4 g (0.05 mole) of 4-(1,3-dioxo-hexahydro-2-isoindolinyl)phenylacetonitrile and 40 ml of dimethyl sulphoxide was warmed to 50° C. in a flask equipped with a stirrer and a thermometer. 1g (0.025 mole) of sodium borohydride was added to the mixture over a period of 10 minutes and the mixture was then warmed at 50° C. for a further 6 hours. The reaction mixture was then poured into ice-water and the mixture was acidified with dilute hydrochloric acid to give 6.7 g of crude crystals.

These 6.7 g of crude crystals were mixed with 75 ml of acetic acid and 9.5 g of zinc. Maintaining the temperature not above 20° C., 50 ml of concentrated hydrochloric acid were then added over a period of 30 minutes. The mixture was allowed to react at 20° C. for 2 hours and was the filtered. The filtrate was poured into 200 ml of water to precipitate crystals, which were then washed with water to give 5.5 g of these crystals.

These 5.5 g of crystals were placed into a mixture of ethanol, water and sodium hydroxide and the resulting mixture was refluxed, with heating, for 3 hours. After cooling the mixture, it was acidified with dilute hydrochloric acid and the crystals which precipitated were collected by filtration, washed well with water, dried and recrystallized from a mixture of ethanol and petroleum ether, to yield 5.3 g of 4-(1-oxo-hexahydro-2-isoindolinyl)phenylacetic acid, melting point 157°–159° C.

EXAMPLE 16

Aluminium α-[4-(1-oxo-4,7-dihydro-2-isoindolinyl)phenyl]propionate (Compound 7)

A mixture of 8.37 g (0.03 mole) of α-[4-(1-oxo-4,7-dihydro-2-isoindolinyl)phenyl]propionic acid and 30 ml of water was stirred for about 1 hour. At the end of this time, a solution of 2.41 g (0.01 mole) of aluminium chloride hexahydrate in 50 ml of water was added to the resulting solution. The white precipitate which was produced was collected by filtration and washed with 75 ml of water. The resulting white solid was then dried at 105° C. for 4 hours. There were obtained 9.0 g of a white solid, sparingly soluble in most organic solvents, slightly soluble in dimethyl sulphoxide and having a melting point above 300° C.

Calculated for $(C_{17}H_{16}NO_3)_3Al$: Al, 3.09%. Found: Al, 3.15%.

IR Spectrum: 3000–2700 cm$^{-1}$ (—OH), 1680 cm$^{-1}$ (C = O), 1670 cm$^{-1}$ (C = O).

EXAMPLE 17

Aluminium α-[4-(1-oxo-4,7-dihydro-2-isoindolinyl)phenyl]propionate (Compound 7)

A mixture of 0.5 g (0.0018 mole) of α-[4-(1-oxo-4,7-dihydro-2-isoindolinyl)phenyl]propionic acid, 0.072 g (0.0018 mole) of sodium hydroxide and 5 ml of water was stirred for about 1 hour. At the end of this time, a solution of 0.434 g (0.0018 mole) of aluminium chloride hexahydrate in 10 ml of water was added dropwise at room temperature to the mixture. The white precipitate produced was collected by filtration, washed with 75 ml of water and dried at 105° C. for 4 hours. There was obtained 0.45 g of a white solid, which was sparingly soluble in most organic solvents and slightly soluble in dimethyl sulphoxide, and which had a melting point over 300° C.

Calculated for $(C_{17}H_{16}NO_3)_3Al$: Al, 3.09% Found: Al, 3.08%.

IR Spectrum: 1680 cm$^{-1}$ (C = O), 1670 cm$^{-1}$ (C = O).

EXAMPLE 18

Bismuth α-[4-(1-oxo-4,7-dioxo-2-isoindolinyl)phenyl]propionate (Compound 8)

To a stirred mixture of 1.38 g (0.005 mole) of α-[4-(1-oxo-4,7-dihydro-2-isoindolinyl)phenyl]propionic acid, 0.265 g (0.0025 mole) of soda ash and 100 ml of water was added dropwise at room temperature a solution of 0.808 g (0.0017 mole) of bismuth nitrate in 50 ml of water. The white precipitate which was produced was allowed to stand for about 2 hours. After filtration and washing with water, the white precipitate was dried at 105° C. for about 4 hours. There were obtained 1.66 g of a white solid having a melting point above 300° C.

Calculated for $(C_{17}H_{16}NO_3)_3Bi$: Bi, 19.8%. Found: Bi, 19.53%.

IR Spectrum: 1670 cm$^{-1}$ (C = O).

Following substantially similar procedures to those described in the above Examples, the following compounds were also prepared:

Ethyl α-[4-(1-oxo-4,7-dihydro-2-isoindolinyl)phenyl]propionate (Compound 9)
   m.p. 134°–135.5° C.;

α-[4-(1-oxo-4,7-dihydro-2-isoindolinyl)phenyl]propionamide (Compound 10)
   m.p. 229°–231° C.;

α-[4-(1-oxo-4,7-dihydro-2-isoindolinyl)phenyl]propionic acid morpholide (Compound 11)
   m.p. 169°–171° C.;

α-[4-(1-oxo-4,7-dihydro-2-isoindolinyl)phenyl]propionic acid diethylamide (Compound 12)
   m.p. 159°–161° C.;

Sodium α-[4-(1-oxo-4,7-dihydro-2-isoindolinyl)phenyl]propionate (Compound 13)
   m.p. < 265° C. (decomposition).

We claim:
1. Aluminium α-[4-(1-oxo-4,7-dihydro-2-isoindolinyl)phenyl]propionate.
2. Bismuth α-[4-(1-oxo-4,7-dihydro-2-isoindolinyl)phenyl]propionate.

* * * * *